United States Patent [19]

Higo et al.

[11] Patent Number: 5,280,724
[45] Date of Patent: Jan. 25, 1994

[54] ULTRASONIC INSPECTION METHOD FOR DETECTING DEFECTS IN SOLID OBJECTS

[75] Inventors: Yakichi Higo, No. 5-3-1-101, Yagumo, Meguro-ku, Tokyo; Shigenori Kazama, Yokohama, both of Japan

[73] Assignees: Nissan Motor Co., Ltd., Yokohama; Yakichi Higo, Tokyo, both of Japan

[21] Appl. No.: 972,067

[22] Filed: Nov. 5, 1992

Related U.S. Application Data

[63] Continuation of Ser. No. 505,324, Apr. 5, 1990, abandoned.

[30] Foreign Application Priority Data

Jun. 22, 1989 [JP] Japan ................................ 1-160080

[51] Int. Cl.⁵ .................... G01N 29/10; G01N 29/24
[52] U.S. Cl. ........................................ 73/624; 73/625; 73/628; 73/641; 310/336
[58] Field of Search ............... 73/625, 626, 627, 628, 73/641, 600, 644, 624, 634, 622; 310/336

[56] References Cited

U.S. PATENT DOCUMENTS

| | | |
|---|---|---|
| 2,784,325 | 3/1957 | Halliday et al. |
| 3,147,169 | 1/1964 | Albertson ............... 73/630 |
| 3,472,065 | 10/1969 | Maxwell. |
| 3,978,714 | 9/1976 | Shraiber et al. ........ 73/625 |
| 4,019,373 | 4/1977 | Freeman et al. ....... 73/644 |
| 4,235,112 | 11/1980 | Kaiser ..................... 73/634 |
| 4,242,744 | 12/1980 | Rottman ................. 73/644 |
| 4,275,598 | 6/1981 | Engl ....................... 73/641 |
| 4,432,231 | 2/1984 | Napp et al. ............. 73/644 |
| 4,437,348 | 3/1984 | Sasaki ..................... 73/625 |
| 4,457,176 | 7/1984 | Scholz .................... 73/628 |
| 4,689,996 | 9/1987 | Hüschelrath ........... 73/644 |
| 4,699,007 | 10/1987 | Kawashima et al. .... 73/641 |
| 4,760,738 | 8/1988 | Katamine ............... 310/336 |

FOREIGN PATENT DOCUMENTS

| | | |
|---|---|---|
| 0379898 | 3/1986 | Austria . |
| 0228720 | 7/1987 | European Pat. Off. . |
| 0284689 | 10/1988 | European Pat. Off. . |
| 1093472 | 5/1955 | France . |
| 2281567 | 3/1976 | France . |
| 63-120252 | 6/1988 | Japan . |
| 0297057 | 12/1990 | Japan ..................... 73/627 |
| WO83/02844 | 8/1983 | PCT Int'l Appl. . |
| 2033579 | 5/1980 | United Kingdom . |

Primary Examiner—Hezron E. Williams
Assistant Examiner—Rose M. Finley
Attorney, Agent, or Firm—Pennie & Edmonds

[57] ABSTRACT

A non-destructive, non-invasive arrangement is provided for detecting defects, such as voids, or poorly adhering layers in solid objects and laminated materials. A sensing signal is emitted by one transducer and received by two others. All of the sensors are disposed in a housing unit. The difference between the received signals is used to indicate a defect in the work piece proximate one of the transducers.

27 Claims, 9 Drawing Sheets

ULTRASONIC INSPECTION METHOD FOR DETECTING DEFECTS IN SOLID OBJECTS

This is a continuation of application Ser. No. 07/505,324, filed Apr. 5, 1990, now abandoned.

BACKGROUND OF THE INVENTION

1. Field of the Invention

The present invention relates to a non-destructive means for detecting defects, such as voids, or poorly adhering layers in solid objects and laminated materials. More specifically, the instant invention relates to an ultrasonic scanning arrangement which includes ultrasonic emitting and receiving transducers which are disposed in a housing, and via which an object can be non-invasively inspected for defects.

2. Description of the Prior Art

In the art of ultrasonic detection, various methods are known for non-destructively inspecting solid objects. Among these methods are an ultrasonic transmission technique, a reflection technique, and an ultrasonic resonance technique. One or more of the above methods is selected, depending usually upon the test conditions, and the number of transducers to be used in the test device.

The sensing methods may be further sub-divided into a so called vertical method, angular method, immersion method, panel wave method, surface wave method, transmission method, thickness detection method, the holographic imaging method, and the defect detection arrangement method.

Some prior art detection methods are disclosed in detail in The Third Edition of The Steel handbook Volume IV "Alloys: Tests and Analysis" Oct. 30 1972, Published by Maruzen Co. Ltd. on pages 447-448 under the heading "Non-destructive Tests".

In FIG. 1 an example is given of a sensor assembly 51 according to the prior art. A housing unit 52, includes an insulating member 53 which is disposed in the blind end of a elongate bore, a spring 54 and an ultrasonic transducer 55. The spring is arranged to bias the ultrasonic transducer 55 against an object 11 under test.

Within the interior of the housing unit 52, a lateral buffer member 56 is disposed, which serves to maintain the in position while insulating the housing unit 52 from the ultrasonic transducer 55.

In detection operations using the FIG. 1 device, it is common to use the resonance method or the reflection method. On the other hand, in cases where two transducers are provided, it is known to employ the transmission technique.

As is well known, with these methods, the reflected or the transmitted signals and/or resonance frequencies are analyzed in order to determine the characteristics of the object to be tested. In the above techniques however, problems have been encountered in that the strength, and general characteristics of the received measurement signals are rather strongly influenced by the pressure with which the transducer assembly is maintained in engagement with the object to be tested. For this reason, considerable skill on the part of the operator, has been required in order to obtain reproducible readings. This has tended to limit the applicability of these methods and has prevented more general use.

Accordingly, there has been a need to provide a technique of holding an ultrasonic transducer in engagement with an object to be tested in a manner which alleviates the need for a high level of skill on the part of the operator.

Another disadvantage encountered in the ultrasonic sensing devices of the prior art lies in the fact that, a single transducer is usually used for both emitting and receiving the inspection signal. Because of this double function, compromises must be made in the construction of the transducer, in order to allow it to serve equally well as an emitter and receiver. Another problem with this arrangement is that the transducer must be switched very rapidly between the emitting and receiving modes, and thus renders the signal sending and receiving sections of the control device, complex.

In view of the above problems, a method, which is disclosed in JP-A-63-120252, was developed for detecting the presence or absence adhesion between the layers of laminated material, and for determining the bonding strength of an adhesive when it is present.

In the above disclosed device the problem remains that a rather high level of skill is still required of the user, in order to obtain satisfactory reproducible results.

SUMMARY OF THE INVENTION

It is one object of the instant invention to provide a non-destructive non-invasive inspection arrangement which enables an object to be checked for internal defects, which obviates the need for a high the level of operator skill and which enables reproducible results to be readily obtained.

It is a further object of the instant invention to provide an easy to use, non-destructive non-invasive inspection arrangement for determining the presence and strength of bonding between layers of a laminated object or material.

In brief, the above objects are achieved by a basic arrangement, wherein a sensor assembly comprising an ultrasonic emitter for emitting an ultrasonic sensing signal towards an object to be tested, two receiving transducers for receiving said ultrasonic sensing signal, and a housing arrangement which hold the ultrasonic emitter and the receiving transducers in a predetermined spaced relationship with respect to one another, is used. The difference between the signals received by the two receiving transducers is used to determine the presence or absence of a defect. In the case the distance each of the receiving transducers and the emitter is not the same, a delay can be applied to the signal from the closer one.

More specifically, a first aspect of the present invention is deemed to comprise a sensing device which features a sensor assembly having: an ultrasonic emitter, the ultrasonic emitter emitting an ultrasonic sensing signal to an object to be tested; a first receiving transducer, the first receiving transducer receiving the ultrasonic sensing signal which is propagated through the object to be tested; a second receiving transducer, the second receiving transducer receiving the ultrasonic sensing signal which is propagated through the object to be tested; and a housing, the housing supporting the ultrasonic emitter, the first receiving transducer, and the second receiving transducer in a predetermined spaced relationship with respect to one another.

A second aspect of the present invention is deemed to comprise an ultrasonic sensing device which features: a plurality of transducers, the plurality of transducers being not less than four, each transducer of the plurality of transducers being capable of emitting and receiving an ultrasonic signal; ultrasonic signal generating means for generating an ultrasonic signal; and selection means for selecting which of the plurality of transducers is to be driven to emit an ultrasonic signal produced by the signal generating means, and which of the remainder of the plurality of transducers are to receive ultrasonic signals and output signals to signal processing means.

A third aspect of the present invention is deemed to comprise a sensing device which features: an ultrasonic emitter, the ultrasonic emitter emitting an ultrasonic sensing signal to an object to be tested; a first receiving transducer, the first receiving transducer receiving the ultrasonic sensing signal after it has propagated through the object to be tested and outputting a first received signal, the first receiving transducer being disposed at a first distance from the ultrasonic emitter; a second receiving transducer, the second receiving transducer receiving the ultrasonic sensing signal after it has propagated through the object to be tested and outputting a second received signal, the second receiving transducer being disposed at a second distance from the ultrasonic emitter; comparing means for comparing the first second received signals from the first and second receiving transducers; and delay means for delaying the first received signal and for compensating for a difference in the first and second distances.

A fourth aspect of the present invention is deemed to comprise a sensor device which features: a housing unit; a plurality of transducers, the plurality of transducers being disposed in the housing unit, not less than one transducer of the plurality of transducers being operable for emitting an ultrasonic sensing signal and not less than two transducers of the plurality of transducers being operable for receiving an ultrasonic signal; and pressure sensing means for sensing the pressure with which the not less than one transducer is forced into contact with a test piece.

DETAILED DESCRIPTION OF THE PREFERRED EMBODIMENTS

Figure 1:
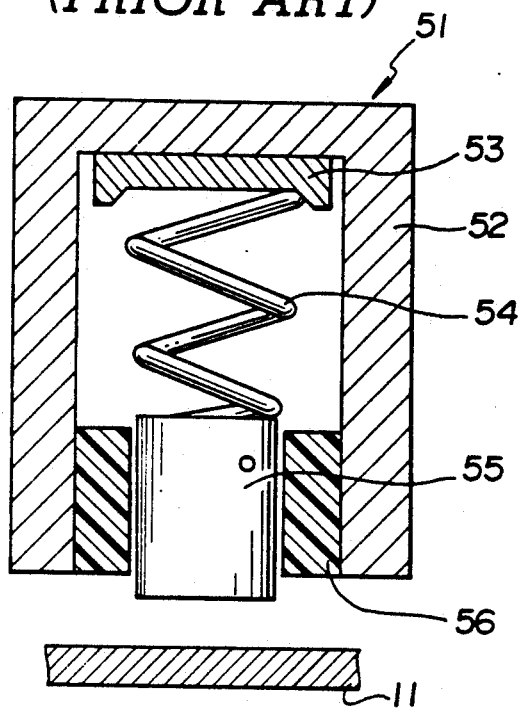
FIG. 1 is cross-section view of a sensor assembly according to the prior art.
Figure 2:
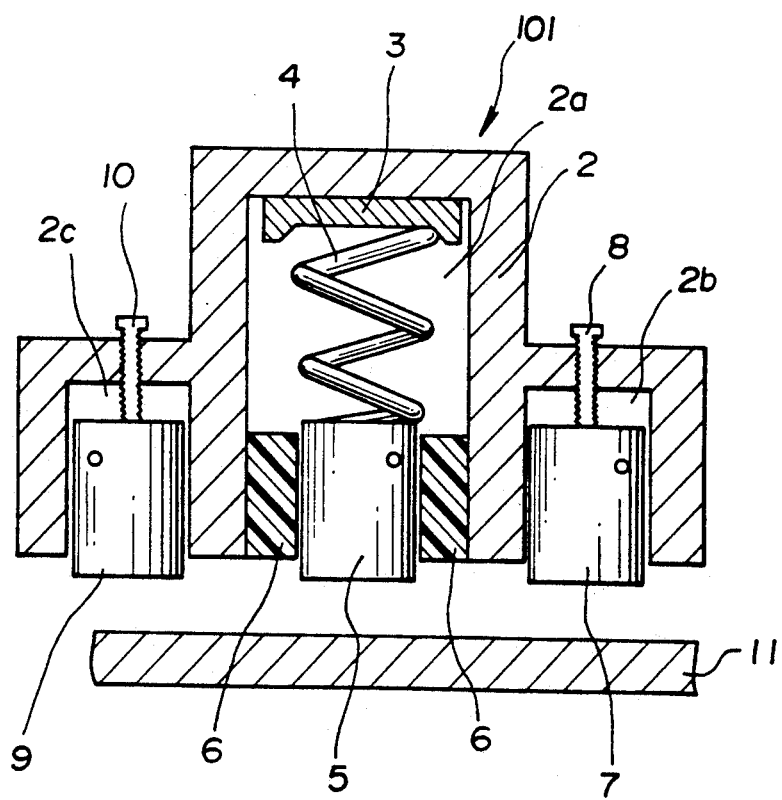
FIG. 2 is a cross-section view of a sensor assembly according to the first embodiment of the present invention.

FIG. 2 shows a sensor assembly 101 according to a first embodiment of the instant invention. The sensor assembly 101 comprises a housing unit 2, having an emitter receiving bore or cavity 2a within which an ultrasonic emitter 5, which is adapted for emitting an ultrasonic sensing signal, is disposed. Receiving transducers 7 and 9, which are adapted for receiving such types of signals, are provided in a pair of transducer receiving bores 2b and 2c.

An insulating member 3, formed of a resilient material, and a spring 4, support the emitter 5 within the bore 2a. The upper end of the spring 4 is arranged to engage the insulating member 3, which is provided on the upper inside surface of the emitter receiving cavity 2a. The lower end of the spring 4 supports the ultrasonic emitter 5. A lateral buffer 6 is disposed in the mouth of the bore 2a in a manner to surround the emitter 5 and isolate the same from the housing unit 2.

The receiving transducers 7, 9 are connected to the housing unit 2 by means of height adjuster screws 8, 10 which serve to determine the positions of the receiving transducers 7 and 9 within the bores 2b, 2c.

The ultrasonic emitter 5 and the receiving transducers 7 and 9 are arranged in a manner such that the spacing therebetween is fixed in the horizontal directions. On the other hand, the heights of the receiving transducers 7 and 9, are adjustable (viz., the transducers are adjustable in the vertical direction).

For simplicity of disclosure, the embodiment of FIG. 2 comprising the single ultrasonic emitter 5 and the two receiving transducers 7 and 9, has been chosen to illustrate the principles of the instant invention. It will be understood, however, that arrangements wherein more receiving and or emitting transducers are within the scope of the invention.

With this arrangement, when the sensor assembly 101 is employed in an inspection/detection operation, it is held against the surface of the object to be tested, so that the receiving transducers 7 and 9 are in firm contact therewith. In this state, the ultrasonic emitter 5 is urged into engagement with surface of the object to be tested, by means of the spring 4. While the sensor assembly 1 is maintained in this state, an ultrasonic sensing signal is emitted from the ultrasonic emitter 5. This ultrasonic sensing signal propagates through the object to be tested and is picked up by the receiving transducers 7 and 9, which are arranged to be equidistant from the ultrasonic emitter 5.

Under the above conditions, if the object 11 under inspection is free of defects, the signals received by the respective receiving transducers 7 and 9 are essentially identical. If, on the other hand, a defect or inconsistency exists in the vicinity of one of the receiving transducers 7 and 9, the received signals exhibit a difference.

In FIG. 3 the emitter 5 and the receiving transducers 7 and 9 are schematically depicted in engagement with an object 11 under test which contains a defect or void 12.

Given that the positions of the receiving transducer 9, emitter 5, and the receiving transducer 7 in the direction indicated by the arrow in FIG. 3, are X1, X and X2 respectively; the position of the defect is given as Y; and the ultrasonic signals received by the respective receiving transducers 9 and 7 are f(X1) and f (X2), respectively, then it can be demonstrated that under these conditions:

If $Y<X1<X<X2$, $X1<X<X2<Y$ then $f(X1)=f(X2)$;
If $X1<Y<X<X2$ then $f(X1)<f(X2)$;
If $X1<X<Y<X2$ then $f(X1)>f(X2)$.
Given that:

$$Z=f(X1)-f(X2) \quad (1)$$

Figure 3A:
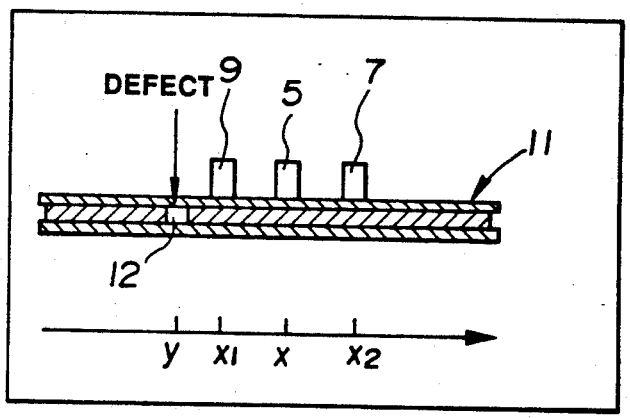
FIG. 3a is a schematic depiction of a sensor assembly according to the invention in contact with an object which includes a defect, wherein the positions of the defect, and the respective transducers are indicated.
Figure 3B:
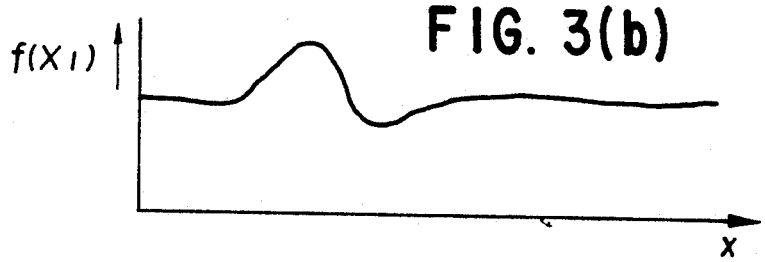
FIGS. 3b and 3c are timing charts which graphically show the fluctuations in the signals produced by the receiving transducers 7 and 9 as they pass the defect.
Figure 3C:
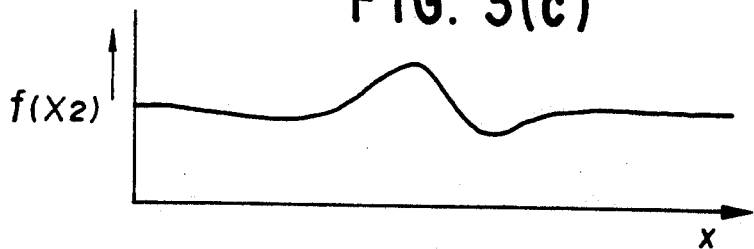
Figure 3D:
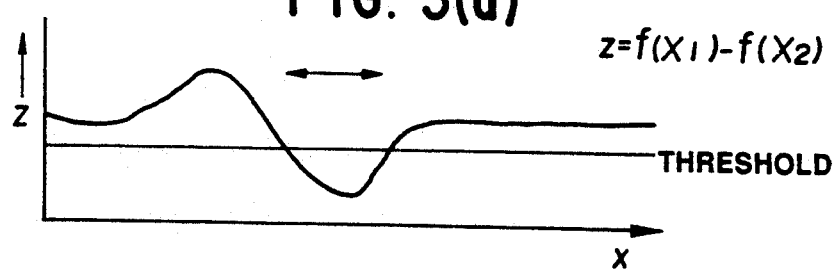
FIG. 3d is a timing chart showing the manner in which the defect is detected using a value Z (derived by subtracting the data of FIGS. 3(c) and 3(d) from one another), with a predetermined threshold level.

The deviation of Z in either the positive or negative directions by more than a predetermined amount will indicate the presence of a defect in the vicinity of the sensor assembly. In practice, to simplify the operation required in a sensor signal processor 16, to make the defect determination, it is adequate to set a threshold or slice value, as illustrated in FIG. 3d, and to determine if the value of Z crosses the same.

The characteristic of this type of sensing operation which sets it above those of the prior art is that, since the signals of the respective receiving transducers 7 and 9 are compared only to each other in order to obtain the value Z, volume or frequency deviations, or distortion, in the signal output of the ultrasonic emitter 5, have no tendency to influence the value Z in such a manner as to cause a false indication of the presence of a defect 12 in the object 11. Thus, the dependability, of the sensing signal obtained, is dramatically increased.

Figure 4:
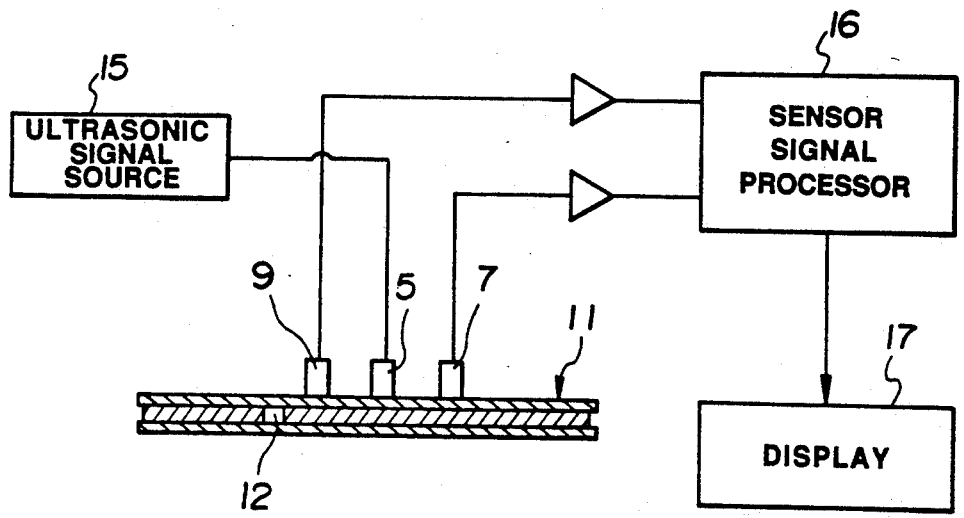
FIG. 4 is a schematic depiction of a sensing arrangement according to the invention.

In FIG. 4 the sensor assembly 101 of FIG. 2 and the associated circuitry are depicted schematically. The ultrasonic emitter 5 is coupled to an ultrasonic signal source 15, by which it is driven to output the ultrasonic sensing signal. This signal, as has been mentioned above, is propagated through the object 11 under test. This propagated ultrasonic sensor signal is picked up by the receiving transducers 7 and 9, by which it is converted into an electronic signal, which is, in turn, supplied to the sensor signal processor 16.

Within the sensor signal processor 16, the signal received from one of the receiving transducers 7 and 9, is treated as a reference signal to which that of the other is compared, in order to discern the presence of a defect 12. Thereafter, the result of the determination, made by the sensor signal processor 16, as to whether or not a defect 12 is present, is shown on a display 17.

With this arrangement, since the sensor signal processor 16 compares the sensed signals of the receiving transducers 7 and 9 directly rather than using a fixed value, the quality of the contact, between the object to be tested and the sensor assembly 101, is inherently compensated for in the data processing stage. Therefore, it is possible when using the sensor assembly 101 according to the invention, to use analog processing to discern the presence of a defect.

For example, by employing an R.M.S. meter in connection with a differential input circuit in the sensor signal processor 16, it is possible, using the sensor assembly 101 according to the present invention, to provide a defect detection unit which is easier to use, more dependable, and simpler than the ultrasonic sensor assemblies of the prior art. Moreover, with this arrangement, these advantages are realized in a device which provides a real time indication of defects in the object under test.

A further advantage of the ultrasonic sensing arrangement of the instant invention, is the fact that the sensing signal is no longer limited to the pulsed signals commonly used in the prior art arrangements and can be tailored to suit the material, and to provide a more accurate picture of the internal characteristics of the object under test. For example, since the wave shape and frequency, of the sensing signal, is not limited, it may be deemed desirable to provide a signal which consists of random noise within a selected frequency band, or pararandom wave forms at selected frequencies. Sensing signals in the frequency band of 0.1 Hz to 10 MHz have been used with good results.

Figure 5:
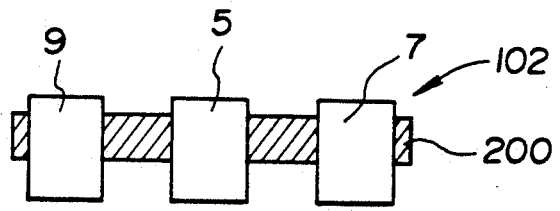
FIG. 5 is a cross-section of a sensor assembly according to a second embodiment of the invention.

FIG. 5 shows a second embodiment of a sensor assembly 102 according to the invention. It has been found that, in cases where surface of the object to be tested is perfectly flat, it is possible to dispense with the spring 4 and the other buffer members and simply arrange a housing unit 200 such that it maintains the ultrasonic emitter 5 and the receiving transducers 7 and 9 in such a manner that their emitting and sensing surfaces lie in a common plane.

On the other hand, since it is extremely difficult to ensure that the surfaces of the ultrasonic emitter 5 and receiving transducers 7 and 9 lie perfectly within a common plane, and that the surface of the object to be tested is perfectly flat, it has been found that, to assure an accurate detection signal, it is preferable that an arrangement wherein the ultrasonic emitter 5 is resiliently mounted, be employed.

Figure 6:
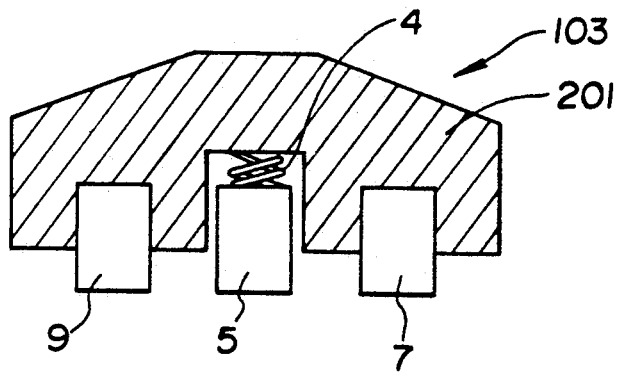
FIG. 6 is a cross-section of a sensor assembly according to a third embodiment of the invention.

In a sensor assembly 103, according to the third embodiment of the invention (depicted in FIG. 6) the arrangement of the elements is essentially the same as that of the first embodiment with the exception that the height adjuster screws 8 and 9 are omitted, and the receiving transducers 7 and 9 are affixed directly to the housing unit 201. The ultrasonic emitter 5 is, as in the first embodiment, resiliently coupled to the housing unit 201. Thus, although the heights of the receiving transducers 7 and 9 are not adjustable as in the first embodiment, they essentially define only two contact points on a line on the surface of the object to be tested, when the sensor assembly is held in contact therewith. The ultrasonic emitter 5 is resiliently urged into contact with the surface of the object under test by the spring. Thus, unevenness or curvature of the surface, of the object to be tested, is absorbed or compensated for by the spring 4. Therefore, regardless of the curvature of the surface of the object to be tested, the operation for determining its internal characteristics can be carried out accurately.

Figure 7A:
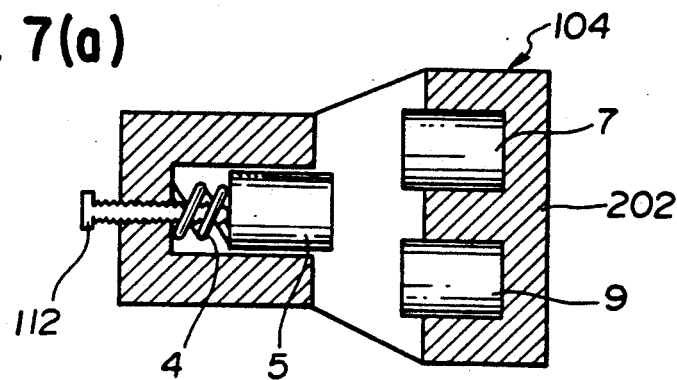
FIGS. 7a and 7b are a cross-sectional plan and side elevational views of a sensor assembly according to a fourth embodiment of the invention.
Figure 7B:
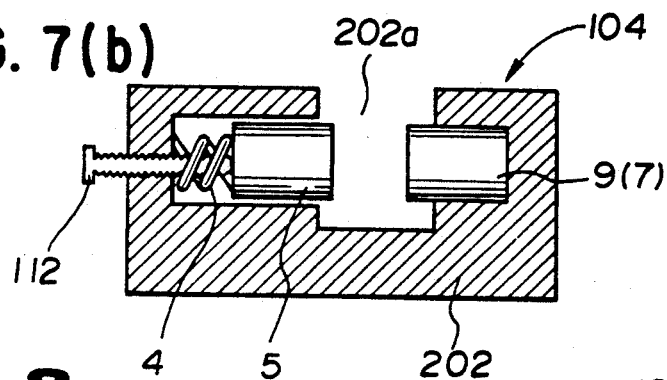

In FIGS. 7a and 7b a fourth embodiment of a sensor assembly according to present invention is depicted. The sensor assembly 104 according to the fourth embodiment differs from that of the first and second embodiments in that the housing unit 202 defines a gap 202a, and the ultrasonic emitter 5 is arranged so as to oppose the receiving transducers 7 and 9, across said gap 202a.

With this arrangement the receiving transducers 7 and 9 pick up the ultrasonic signal emitted from the ultrasonic emitter 5, from the opposite side of the object to be tested. In this arrangement the ultrasonic emitter 5 is supported, on the housing unit 202, by means of a pressure adjuster screw 112, by which the position of the ultrasonic emitter 5 can be adjusted with respect to the receiving transducers 7 and 9, and a spring 4. Thus, the overall arrangement is somewhat similar to that of a C-clamp.

It will be noted that the mode of contact between the ultrasonic emitter 5 and the receiving transducers 7 and 9, and the object to be tested is not limited to direct contact. With the embodiments disclosed the same effect can be achieved as the prior art arrangements wherein oil or water have been used and/or the arrangements wherein rubber tires have been utilized.

Figure 8:
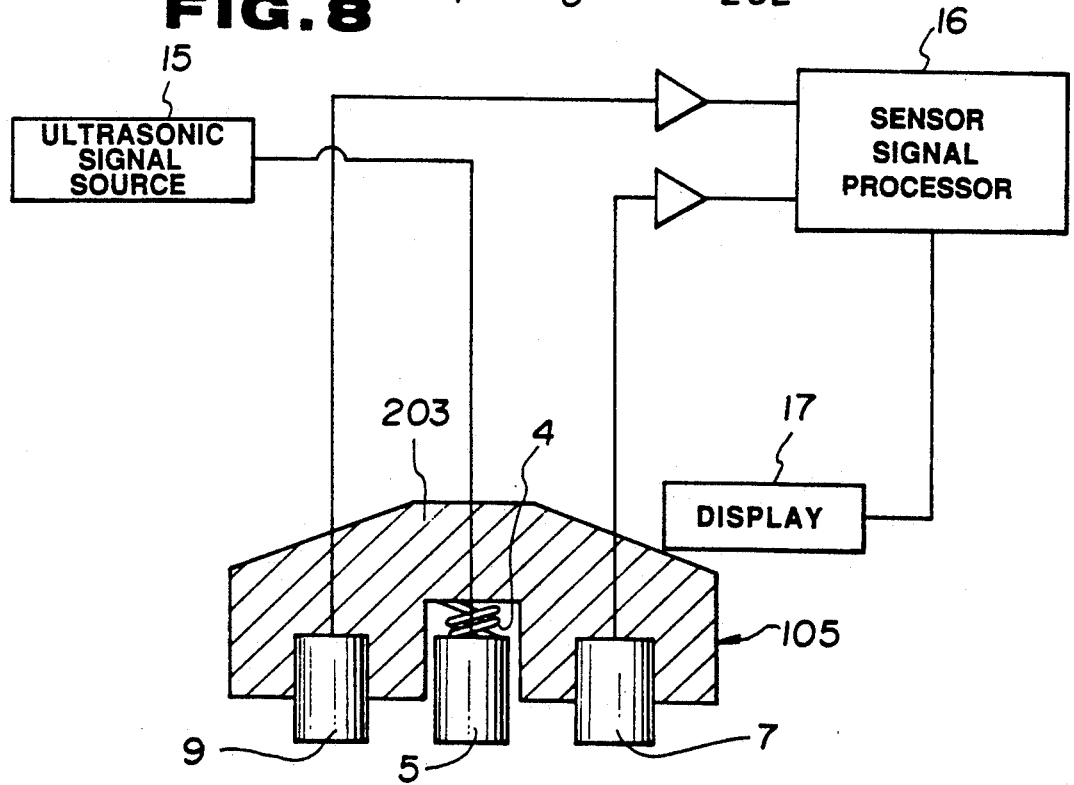
FIG. 8 is a cross section of a sensor assembly according to a fifth embodiment of the invention, with a sensing circuit, associated therewith, depicted schematically.

FIG. 8 shows a sensor assembly 105, according to a fifth embodiment of the present invention. This embodiment is essentially identical to the first and third ones with the major exception that the display 17 is mounted directly on the housing unit 203.

This arrangement has the advantage that the operator of the sensing device can see the display 17 indicating the internal condition of the object to be tested, in real time, without having to take his (or her) eyes from the object under test. Thus, it is easy to visually pinpoint the spot, on the surface the object to be tested, beneath which a defect is present.

A further advantage of this arrangement is that the display can indicate to the user exactly when and where, on the object, the proper contact between the sensor assembly and object to be tested becomes inadequate to provide an accurate indication of the internal state of the object to be tested, in other words, when the output of the receiving transducers 7 and 9 fall beneath a predetermined value.

Figure 9:
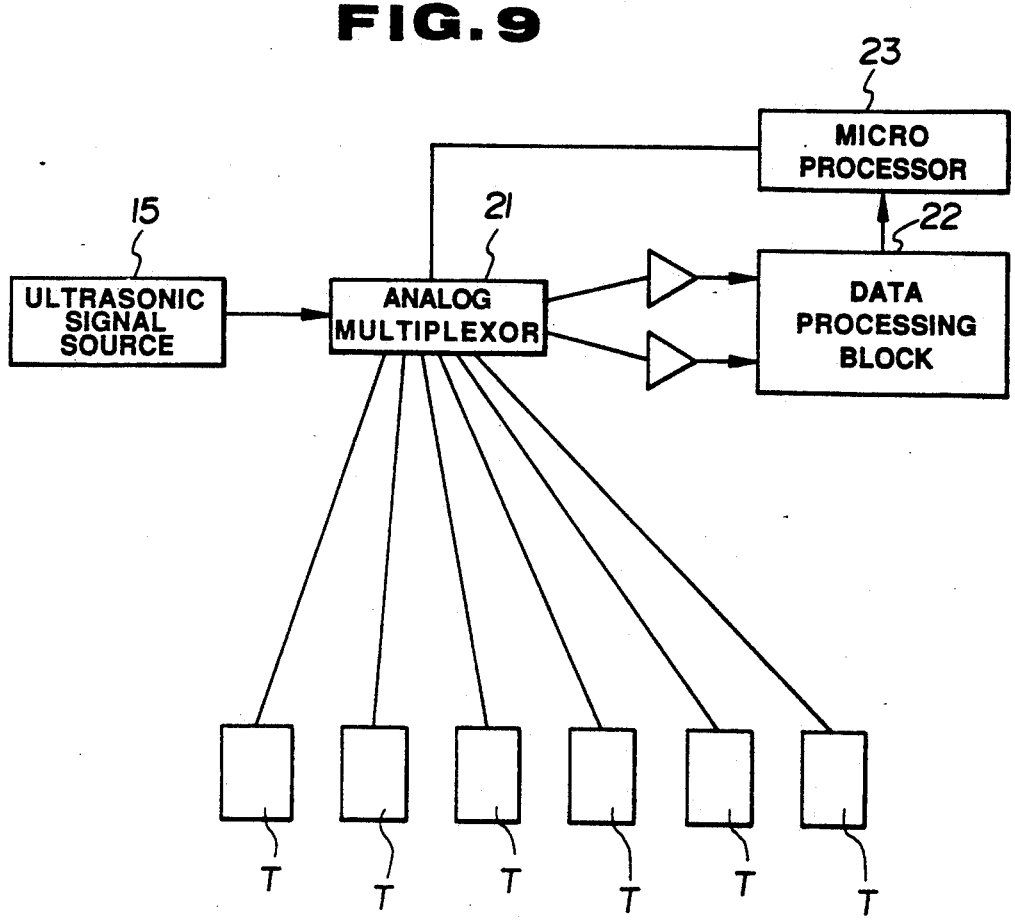
FIG. 9 is as schematic depiction of a sensing arrangement according to a sixth embodiment of the invention.

In the sixth embodiment of the invention, shown in FIG. 9, another data processing circuit arrangement is exemplified. In this arrangement, an analog multiplexor 21 is coupled with a plurality (six in this particular case) transducers T. The data from the analog multiplexor 21 is supplied to the data processing block 22 and from there to the micro-processor 23.

The transducers T are of the type that can both output and receive an ultrasonic signal. With this arrangement, the multiplexer can send and receive signals from a group selected from among any of the transducers T. For example, the multiplexer may operate one of the transducers T as an ultrasonic emitter, and the two adjacent thereto as the receiving transducers. Thus, the transducers are operated in groups of three, or "triplets", and any three transducers can be incorporated into a triplet.

With this arrangement, the triplets are sequentially selected from the plurality of transducers, and their signals are processed to determine whether a defect, is present in the vicinity of any triplet of the transducers T. Thus, a large portion of the surface of the object can be quickly and accurately inspected, without moving the individual transducers T.

Another advantage of this embodiment is that, since the transducers do not need to be moved across the surface of the object to be tested, mechanical instability, in the connection between the transducers and the object to be tested, is eliminated.

Still a further advantage of this embodiment is that, even if a defect lies directly beneath an emitting transducer, the situation wherein essentially identical signals are received by the adjacent receiving transducers, when another triplet is selected the transducer which previously was arranged to emit becomes a receiving transducer. Accordingly, signal Z undergoes a change which indicates a defect and accurate inspection is assured.

As will be apparent to those skilled in the art, although in the FIG. 9 embodiment, the triplets or groups of three are used, larger groups are also possible. It will also be understood that although in the above disclosed embodiment the individual transducers must be capable of both emitting and receiving the ultrasonic signal, other embodiments are conceivable wherein at least two of the transducers are arranged to receive the signal only and the remaining transducers are arranged to emit only.

Figure 10:
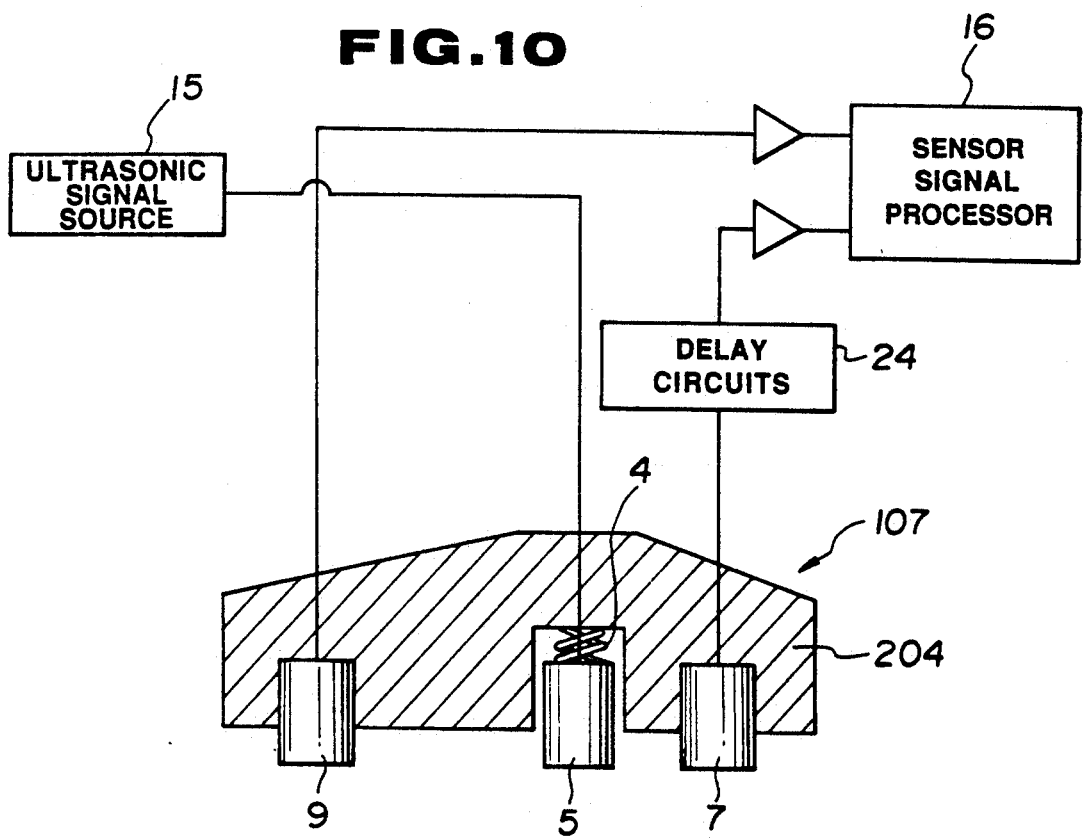
FIG. 10 is a cross-section of a sensor assembly according to a seventh embodiment of the invention, with a sensing circuit, associated therewith, depicted schematically.

In the seventh embodiment of the present invention, shown schematically in FIG. 10, yet another ultrasonic sensing unit circuit is shown. This arrangement is essentially identical to that disclosed in connection with FIG. 4, with the exception that a delay circuit 24 is provided between one or both of the receiving transducers and the sensor signal processor 16.

With this provision, compensation in the signal can be made in cases where the distance between the transducer 9, which does not have the delay circuit 24, and the ultrasonic emitter 5, is greater than that between the receiving transducer 7 which is coupled to the delay circuit 24, and the ultrasonic emitter 5.

This feature is useful in cases where the housing unit 204 of the sensor assembly 107, must for some reason, be constructed such that the distances between the transducers are not equal.

It is also possible with this arrangement, to vary the distance between the receiving transducer 9 and the ultrasonic emitter 5, while adjusting the delay applied by the delay circuit 24 to the signal output of the receiving transducer 7. In such cases, the appropriate offset or delay can be set with the use of a test piece.

Another advantage of this arrangement is that compensation can be made for disparity between the performance characteristics of the respective receiving transducers 7 and 9, which may result from such factors as different types of transducers being used, differing output characteristics of individual transducers in a given production line, or from effects of the housing unit 204 itself on the outputs of the respective transducers.

Since, in the present invention, the ultrasonic emitter 5 and the receiving transducers 7 and 9 are provided separately, it is not necessary to perform the rapid switching operation between the emitting and sending modes, as is required in the ultrasonic sensor assemblies according to the prior art.

Moreover, in the sensing assembly according to the present invention, since there are at least two receiving transducers, a comparison can automatically be made between the signals received by the two, so as to provide an accurate indication of the sensed characteristics of the object to be tested without the need for a great deal of specialized skill on the part of the operator.

Yet another advantage of the ultrasonic sensing arrangement according to the invention is that, since the emitting and receiving transducers are mutually distinct and operate simultaneously and there is no need to generate the pulsed signals perform the rapid switching as in the case of the prior art, the sensing signal output by the ultrasonic emitter 5 does not need to be as strong as in the prior art therefore the performance demands on the ultrasonic signal source 15 are reduced.

Furthermore, since the rapidly pulsed signal is not necessary, the sensing operation can be carried out under more stable conditions than in the prior art methods.

Still another advantage is that both the ultrasonic emitter 5 and the receiving transducers 7 and 9 respectively, do not need to be capable of both sending and receiving the ultrasonic sensing signal. Therefore, the respective transducers can be selected for their efficiency in their respective tasks, rather than making compromises to facilitate both functions.

Another advantage will be readily apparent in the fact that, with the arrangement according to the present invention, a sensing operation can be carried out quickly and in real time.

As mentioned above, the arrangement according to the instant invention may be employed in "wet" arrangements, popular in the prior art, wherein the object to be tested is covered with a layer of oil or water or other substance, or in cases wherein the object to be tested is immersed in a body of fluid or liquid.

It is however a problem in these wet methods and immersion methods, that the fluid tends to soil or have other undesirable effects on the object to be inspected and/or render the inspection process awkward.

Therefore, in the development of the invention, it was conceived to dispense with the fluids used in the "wet" method and, in lieu thereof, dispose a member formed of a solid high polymer material (preferably having a relatively small modulus of elasticity) between the object to be tested and the ultrasonic emitter 5. However, this too has been found to have some disadvantages.

A few of the disadvantages encountered with this method include the problem that it is difficult to ensure a perfect coupling between the ultrasonic emitter 5 and the layer of high polymer material. Due to this problem, the coupling is not satisfactorily stable. Another problem encountered with this method is that, due to the plasticity thereof, there is a tendency for the high polymer material, when force is exerted thereon, to become permanently distorted. When this occurs, the quality of the connection, between the ultrasonic emitter 5 and the high polymer material member, becomes undesirably altered.

Figure 11:
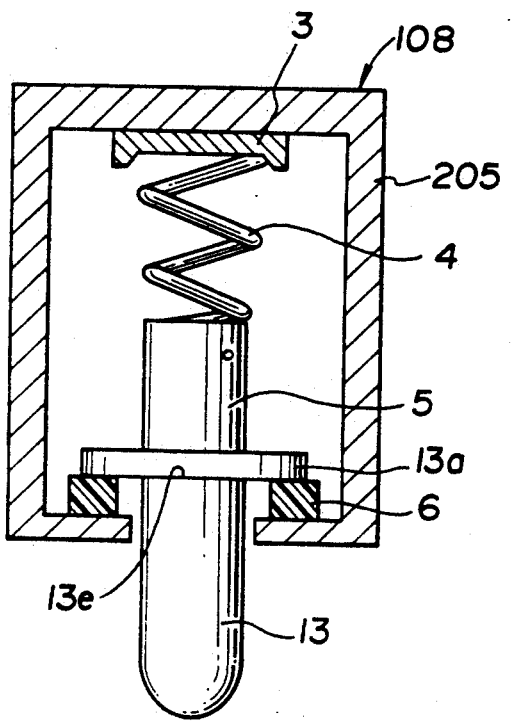
FIGS. 11 and 12 are cross-sections of a sensor assembly according to an eighth embodiment of the invention.
Figure 12:
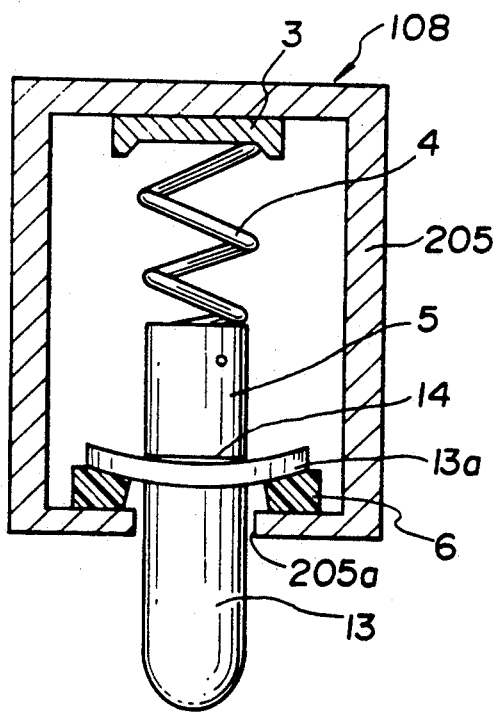

In view of the problem mentioned above, in connection with the permanent damage to the high polymer member, in the eighth embodiment of the invention depicted in FIG. 11, a sensor assembly 108 has been proposed wherein an ultrasound emitting contact 13 is comprised of a high polymer material. In this embodiment, the ultrasound emitting contact 13 is such that it may be easily removed and replaced.

This embodiment spring 4 biases the ultrasonic emitter 5 against an inner side contact surface 13e of the ultrasound emitting contact 13.

The ultrasound emitting contact 13 comprises a flange 13a, which is driven into engagement with a buffer member 6 by the biasing force of the spring 4. The buffer member 6 is disposed between the flange 13a and a radially inwardly extending flange (no numeral) formed at the bottom of the housing unit 205.

In this arrangement, a layer of oil or grease may be provided between the ultrasonic emitter 5 and the inner side contact surface 13e, of the ultrasound emitting contact 13, so as to enhance the connection therebetween.

This embodiment, while providing the improvement wherein the ultrasound emitting contact 13 may be removed and replaced, has been found to suffer the drawbacks that if the engaging force between the ultrasonic emitter 5 and the ultrasound emitting contact 13 is insufficient, there is a tendency for the ultrasound emitting contact 13 to slip and move about with respect to the contact 13 giving rise to problem that the operative coupling between the contact and the emitter becomes inadequate.

These factors tend to result in inconsistency in the ultrasonic sensing signal output by the sensor assembly. On the other hand, if the engaging pressure is too great, there is again the problem of inconsistency or dispersion in the ultrasonic signal output.

For these reasons the problem again arises that rather high operator skill, becomes necessary in order to obtain a dependable and reproducible readings from the sensing unit.

In developing the invention, through experiment and observation, the inventors sought to determine the reason that increasing the engaging pressure beyond a certain value resulted in degradation of the signal output. In these studies it was found that these changes in the characteristics of the sensing signal output came as a result of changes in the shape of the inner side contact surface 13e which engages the ultrasonic emitter 5.

This is because the diameters, of the end of the ultrasonic emitter 5, which engages the ultrasound emitting contact 13, and of the main body of the ultrasound emitting contact 13 must be smaller than that of the flange 13a. This is an indirect result of the fact that the hole 205a in the lower portion of the housing unit 205, must be greater than the outer diameter of the ultrasonic emitter 5, and the main body of the ultrasound emitting contact 13, so the flange 13a, which is relatively thin, must extend past the inner sides of the hole 205a, so as to rest on the buffer member 6.

Because the flange 13a is relatively weak, strong pressure between the ultrasonic emitter 5 and the ultrasound emitting contact 13, has the tendency to cause the outer peripheral portion of the flange 13a to flex upwards, with the result that the inner side contact surface 13e becomes concave. Due to the plasticity of the material of the ultrasound emitting contact 13, this concavity remains. This results in a gap 14 forming between the ultrasonic emitter 5 and the ultrasound emitting contact 13, which reduces the contact area therebetween.

This gap 14 tends to destroy the integrity of the acoustical coupling between the ultrasonic emitter 5 and the ultrasound emitting contact 13.

In order to alleviate the above problem, it was thought to make the flange 13a thicker so as to reduce its tendency to flex. This, however, effectively adds to the overall weight and length of the ultrasound emitting contact 13. Since the high polymer material from which the ultrasound emitting contact 13 is formed has some tendency to absorb the ultrasonic signal emitted by the ultrasonic emitter 5, any increase in the overall length of the ultrasound emitting contact 13 tends to reduce the strength of the ultrasonic signal output to the object to be tested.

Thus, the solution of making the flange 13a thicker, exhibits the drawback of reducing the signal strength of the unit. It has therefore been found that there are limits to the acceptable length of the ultrasound emitting contact 13.

FIGS. 13 to 17 show embodiments which were conceived in order to overcome the above mentioned shortcomings, to realize the goals of providing an arrangement wherein the ultrasound emitting contact 13 is resiliently mounted and the contact between itself and the object to be tested is consistently and stably maintained, and to further ensure efficient transmission of an ultrasonic sensing signal to the object to be tested.

These embodiments are further arranged such that the distance between the contact point of the ultrasound emitting contact 13 on the object to be tested and the contact points of the receiving transducers can be set at an optimal value.

Figure 13:
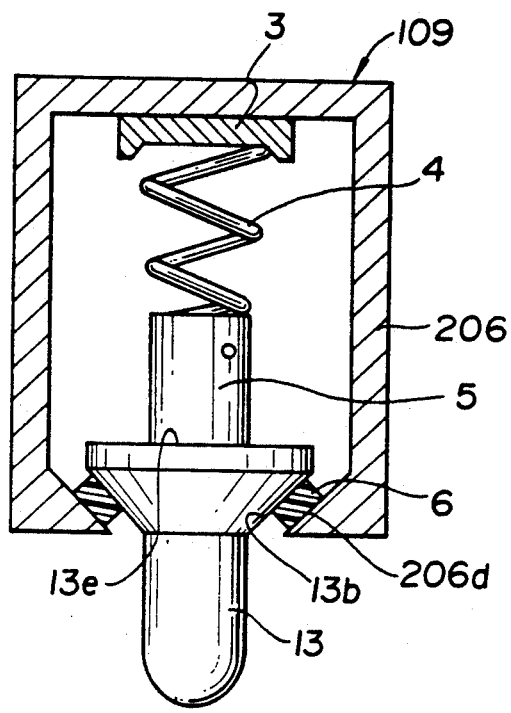
FIGS. 13 and 14 are cross-sections of a sensor assembly according to a ninth embodiment of the invention.
Figure 14:
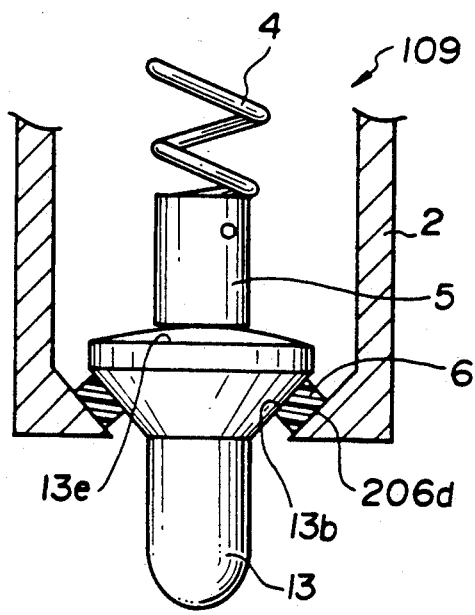

As will be appreciated From FIG. 13, which shows a ninth embodiment of the invention, the housing unit 206 of the sensor assembly 109 is essentially similar to that 205 of the eighth one, and differs in that the inner periphery of the opening defined in the lower side thereof, is formed with a tapered seat 206d. The ultrasound emitting contact 13 in this embodiment is provided with a tapered shoulder 13b which is supportingly spaced from the tapered seat 206d by the buffer member 6.

With this arrangement, the overall contact quality between the ultrasound emitting contact 13 and the ultrasonic emitter 5 is improved. To account for this, it is believed that when the force of the spring 4 drives the ultrasound emitting contact 13 into the tapered seat 206d, there is a tendency for the pressure between the tapered seat 206d and the tapered shoulder 13b to cause the inner side contact surface 13e to distort into the convex configuration shown in FIG. 14. Even if this distortion occurs it does not have any marked detrimental effect on the coupling efficiency between the ultrasonic emitter 5 and the ultrasound emitting contact 13. Therefore, the efficiency and integrity, of the sensing signal emitted thereby, remains high.

One advantageous effect which is believed to be achieved by this convex configuration, is that, in cases where oil or grease is used to enhance the coupling between the ultrasonic emitter 5 and the inner side contact surface 13e, the lubricate can easily enter and tend to fill the annular space which is created.

Whether the convex configuration of the inner side contact surface 13e occurs or not has still not been completely confirmed. Nevertheless, the tendency for the inner side contact surface 13e to become distorted during use is greatly reduced and would appear to be influenced by the angle of the tapered shoulder 13b.

Although any angle of taper for the tapered shoulder 13b and tapered seat 206d is theoretically possible, it has been found that a taper in the range of thirty degrees to sixty degrees is optimum.

It has also been found that, while theoretically any frequency of sensing signal may be employed in the sensing operation using the sensor assemblies according to the invention, frequencies in the range of 0.1 Hz to 10 MHz provide the best results.

Figure 15:
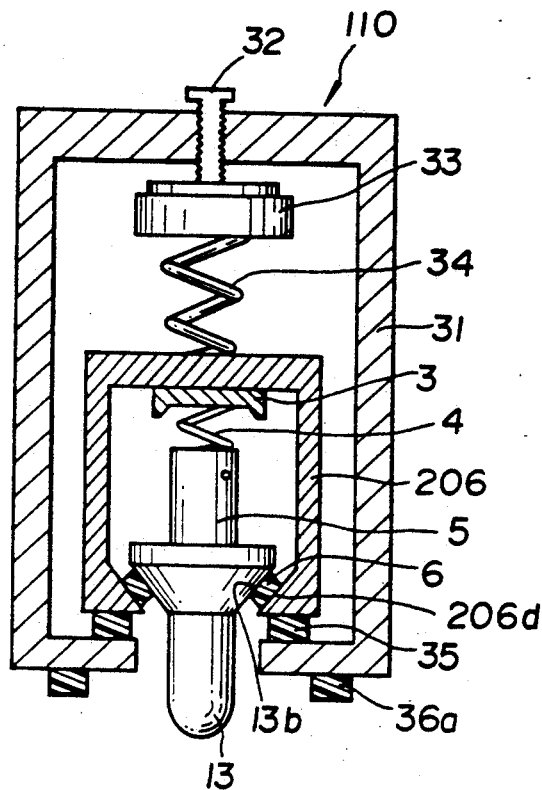
FIG. 15 is a cross section of a sensor assembly according to a tenth embodiment of the invention.

FIG. 15 shows a tenth embodiment of a sensor assembly 110 according to the invention. In this embodiment, the sensor assembly 109, described in connection with the eighth embodiment, is disposed within a second outer housing unit 31. The outer housing unit 31 comprises an outer housing spring 34, one end of which engages the upper side of the housing unit 206, so as to urge it in the engaging direction. At its other end, the outer housing spring 34 engages a pressure sensor 33 which is adjustably connected to the outer housing unit 31, by means of a pressure adjuster screw 32.

At its inner lower surface, the outer housing unit 31 comprises a casing buffer member 35, by which it is resiliently coupled to the housing unit 206, and at its lower side, an outer buffer member 36a, by which it is resiliently isolated from the object to be tested.

In this arrangement the pressure sensor 33 serves to detect the amount of pressure with which the ultrasound emitting contact 13 is being urged into engagement with the object to be tested. This is particularly useful in situations wherein the sensing operation is carried out by robots. Further, due to the fact that the engaging pressure between the ultrasound emitting contact 13 and the object to be tested, can be monitored and adjusted, it is possible to provide consistent and reproducible testing results.

With this arrangement, a further advantage obtained, is that the engaging pressure of the ultrasonic emitter 5 with the object to be tested, through the ultrasound emitting contact 13, can be adjusted independently of the engaging pressures of the receiving transducers 7 and 9. This allows more freedom in adjusting the characteristics of the sensor assembly than is possible in the previous embodiments. It will be noted that the suspension arrangement depicted in FIG. 15 as being applied to the ultrasonic emitter 5, may also be applied in the mounting arrangements of the receiving transducers 7 and 9 so as to facilitate fine tuning of their engaging pressures as well.

It will also be understood, actuating means such as a motor may be disposed within the outer housing unit 31 for the purpose of driving the pressure adjuster screw 32 and adjusting the engaging pressure of the ultrasound emitting contact 13, in accordance with the pressure indicated by the pressure sensor 33.

Figure 16:
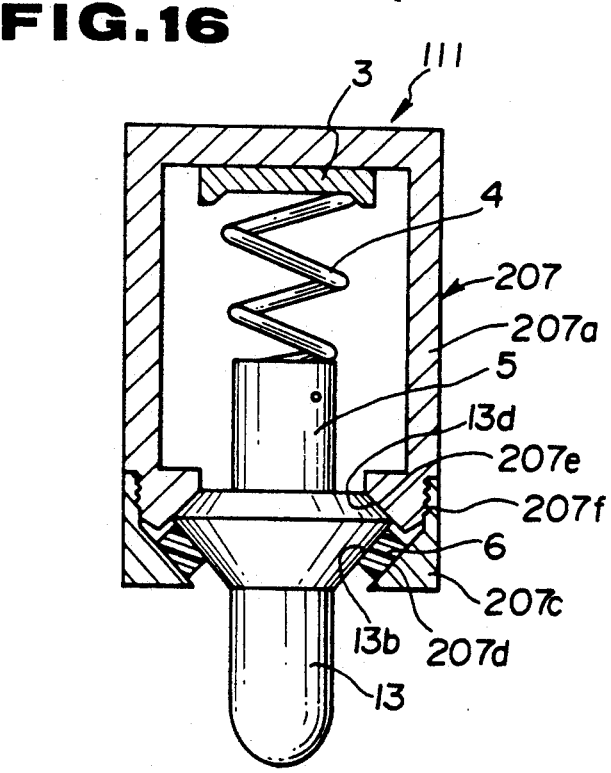
FIG. 16 is a cross section of a sensor assembly according to an eleventh embodiment of the invention.

In the sensor assembly 111 of the eleventh embodiment shown in FIG. 16, the housing unit 207 differs from that 206 of the previous embodiments in that it is divided into upper and lower casing sections 207a, 207c, which are screwed together at a threaded portion 207f.

The upper casing section 207a has an upper tapered seat 207e whose taper is in the opposite direction of that of the lower tapered seat 207d. The upper and lower tapered seats 207e, 207d cooperate to define an essentially V-shaped annular groove around the inner periphery of the lower section of the housing unit 207. The lower tapered seat 207d supports a buffer member 6.

The ultrasound emitting contact 13, according to the eleventh embodiment, is essentially similar in function to that of the previous embodiment except for the fact that, in addition to the tapered shoulder 13b tapering in the downward direction, an upper tapered shoulder 13d is provided, which tapers in the upward direction.

The lower tapered shoulder 13b engages the lower tapered seat 207d through the buffer member 6, while the tapered shoulder 13d engages the upper tapered seat 207e directly.

With this arrangement, while the flexibility in the connection between the housing unit 207 and the ultrasound emitting contact 13 is reduced as the lower casing section 207c is screwed more tightly onto the upper casing section 207a. This tightening of the lower casing section 207c tends to reduce the degree to which the engaging pressure, with which the sensor assembly held in engagement with the object under test, effects the amount of pressure occurring between the ultrasonic emitter 5 and the ultrasound emitting contact 13.

Figure 17:
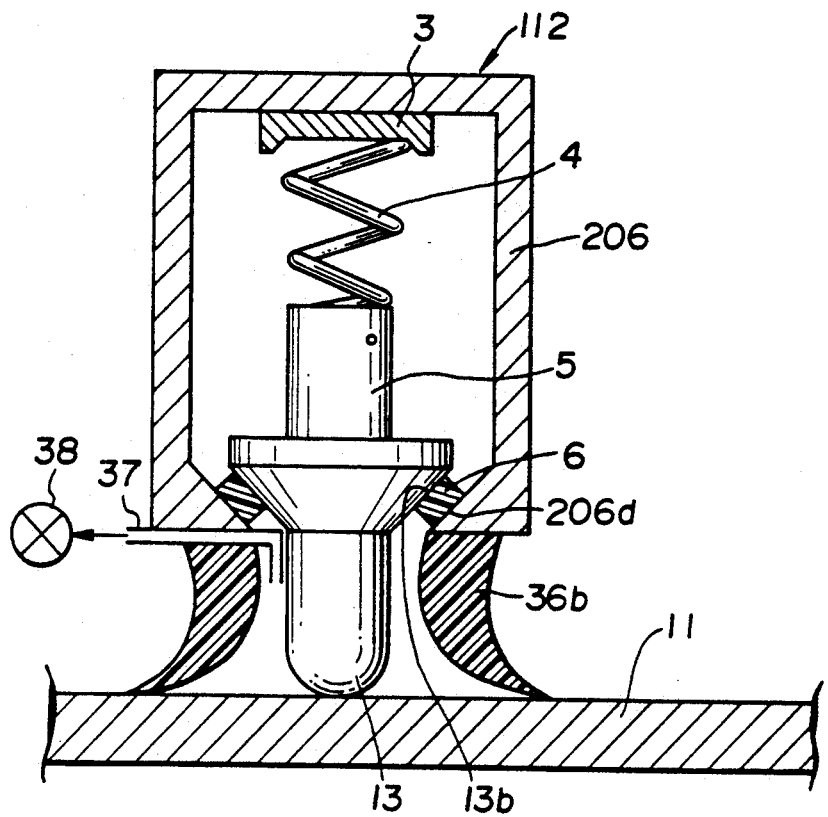
FIG. 17 is a cross section of a sensor assembly according to a twelfth embodiment of the invention.

The sensor assembly 112 of the twelfth embodiment of the invention depicted in FIG. 17 is essentially identical to that depicted in FIG. 13 except that a suction cup 36b has been added to the lower side of the housing unit 206. Therefore, disclosure of the identical portions shall hereinafter be omitted for brevity.

The suction cup 36b has, associated therewith, an evacuation tube 37 and an evacuation pump 38. The evacuation pump 38 is arranged to draw air from chamber defined within the suction cup 36b, when the lower portion thereof is in engagement with the object to be tested. In this manner the sensor assembly is brought into stable firm contact with the surface of the object to be tested, by the negative pressure within the suction cup 36b, so as to provide a stable sensor output. The evacuation pump 38 is also operable for selectively allowing atmospheric pressure to be re-established in the chamber so as to allow the housing unit 206 to be removed from the surface of the object under test.

Figure 18:
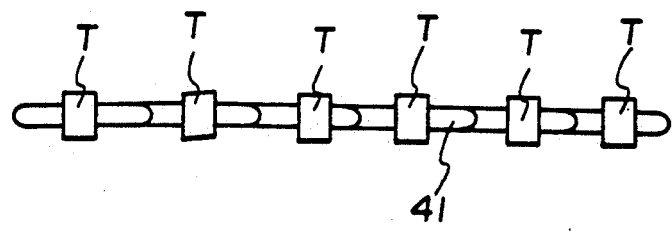
FIG. 18 is a schematic depiction of an alternative arrangement of a transducer holder according to the invention.

In cases where the housing unit 206 is provided with a suction cup buffer member 36b as in the twelfth embodiment, as the engaging pressure of the transducer is determined by the suction cup 36b, it is possible to arrange a plurality of such transducer units, as indicated by the letters T in FIG. 18, on a flexible arm 41.

Although in the embodiments described above, a spring 4 has been disclosed as the resilient body which biases the transducer down onto the top of the surface under test, it will be readily apparent to those skilled in the art that other means may be used to replace or to augment the spring 4 such as adjuster screw, an elastomeric member or the like.

However, it will be noted that in cases where a screw alone is employed in place of the spring 4, particular attention should be made to ensure that the buffer member 6 is formed of a material which exhibits sufficient resiliency as to additionally provide the function of the resilient body (viz., spring 4).

What is claimed is:

1. A sensing device comprising:
   an ultrasonic emitter for emitting an ultrasonic sensing signal to an object to be tested, wherein said ultrasonic emitter directly contacts the object to be tested;
   a first receiving transducer for receiving said ultrasonic sensing signal which propagates through the object to be tested, wherein said first receiving transducer directly contacts the object to be tested;
   a second receiving transducer for receiving said ultrasonic sensing signal which propagates through the object to be tested, wherein said second receiving transducer directly contacts the object to be tested;
   a housing for supporting said ultrasonic emitter and said first and second receiving transducers; and
   a lateral buffer connected to said housing in a manner to surround said ultrasonic emitter and isolate said ultrasonic emitter from said housing,
   wherein said first receiving transducer, and said second receiving transducer being a predetermined spaced relationship with respect to one another, and being aligned along a scanning direction thereof.

2. A sensing device as set forth in claim 1, wherein comparing means is provided for comparing a signal output of said first receiving transducer with a signal output of said second receiving transducer.

3. A sensing device as set forth in claim 1, wherein a contact is disposed between said ultrasonic emitter and the object to be tested.

4. A sensing device as set forth in claim 3, wherein said contact is formed of a high polymer material.

5. A sensing device as set forth in claim 3, wherein said contact is removably attached to said housing.

6. A sensing device as set forth in claim 1, wherein said ultrasonic emitter is resiliently supported in said housing.

7. A sensing device as set forth in claim 3, wherein said ultrasonic emitter is resiliently urged into engagement with said contact.

8. A sensing device as set forth in claim 2, wherein a display means is provided on said housing for displaying a result of the comparison made by said comparing means.

9. A sensing device as set forth in claim 1, wherein said housing comprises a gap into which the object to be tested can be inserted, said ultrasonic emitter and said first and second receiving transducer being arranged so that said ultrasonic emitter is located on one side of said gap and said first and second receiving transducers are disposed on the other side of said gap.

10. A sensing device as set forth in claim 1, wherein said ultrasonic emitter is operatively connected with pressure adjusting means which adjusts the pressure with which said ultrasonic emitter is forced against the object to be tested.

11. A sensing device as set forth in claim 1, further comprising a means for holding said housing on the object to be tested.

12. A sensing device as set forth in claim 11, wherein said holding means comprises a suction cup formed of an elastomeric material, said suction cup being selectively connectable with a source of sub-atmospheric pressure.

13. A sensing device as set forth in claim 1, wherein said ultrasonic emitter is also capable of receiving an ultrasonic sensing signal which is propagated through said object to be tested and wherein said first and second receiving transducers are also capable of emitting an ultrasonic sensing signal to the object to be tested, and further comprising:
   selection means for selecting one of the emitter and the first and second receiving transducers to emit an ultrasonic signal and remaining others of the emitter and the first and second receiving transducers to receive said ultrasonic signal and output signals to a signal processing means.

14. A sensing device as set forth in claim 1, wherein said first and second receiving transducers are disposed at first and second distances from said ultrasonic emitter, and further comprising:
   delay means for delaying one of the signals from said first and second receiving transducers to compensate for a difference in said first and second distance.

15. A sensing device as set forth in claim 1, further comprising pressure sensing means for sensing the pressure with which said ultrasonic emitter is forced into contract with the object to be tested.

16. A sensing device as claimed in claim 15, further comprising resilient means provided between said ultrasonic emitter and said pressure sensing means for resiliently urging said ultrasonic emitter toward the object to be tested.

17. A sensing device as set forth in claim 16, further comprising a contact member which is operatively interposed between said ultrasonic emitter and the object to be tested to provide an operative connection therebetween, said resilient means biasing said contact into contact with the object to be tested.

18. A sensing device as set forth in claim 17, wherein said pressure sensing means is associated with pressure adjusting means, said pressure adjusting means varying the pressure with which the contact is forced into contact with the object to be tested.

19. A sensing device as claimed in claim 1, wherein said housing means comprises an inner housing and an outer housing, wherein said inner housing is resiliently mounted to said outer housing, said ultrasonic emitter being disposed in said inner housing.

20. A sensing device as set forth in claim 1, further comprising an emitter support member by which said ultrasonic emitter is movably supported relative to said housing so as to be in fitting contact with the object to be tested.

21. A sensing device as set forth in claim 1, further comprising a first adjuster connected to said first receiving transducer and said housing such that said first receiving transducer is adjustable relative to said housing and a second adjuster connected to said second receiving transducer and said housing such that said second receiving transducer is adjustable relative to said housing.

22. A sensing device comprising:
   an ultrasonic emitter for emitting an ultrasonic sensing signal to an object to be tested, wherein said ultrasonic emitter directly contacts the objected to be tested;
   a first receiving transducer for receiving said ultrasonic sensing signal which propagates through the object to be tested, wherein said first receiving transducer directly contacts the object to be tested;
   a second receiving transducer for receiving said ultrasonic sensing signal which propagates through the object to be tested, wherein said second receiving transducer directly contacts the object to be tested;
   a housing for supporting said ultrasonic emitter, said first receiving transducer, and said second receiving transducer in a predetermined spaced relationship with respect to one another;
   a first adjuster connected to said first receiving transducer and said housing such that said first receiving transducer is adjustable relative to said housing; and
   a second adjuster connected to said second receiving transducer and said housing such that said second receiving transducer is adjustable relative to said housing.

23. A sensing device as set forth in claim 22, further comprising a lateral buffer which is connected to said housing in a manner to surround said ultrasonic emitter and isolate the same from said housing.

24. A sensing device as set forth in claim 22, further comprising an emitter support member by which said ultrasonic emitter is movably supported relative to said housing and for biasing against the object to be tested.

25. A sensing device for sensing defects in an object by contacting and moving said sensing device on the object in a linear direction, said sensing device comprising:
   an ultrasonic emitter for emitting an ultrasonic sensing signal to an object to be tested;
   a first receiving transducer for receiving said ultrasonic sensing signal which propagates through the object to be tested;
   a second receiving transducer for receiving said ultrasonic sensing signal which propagates through the object to be tested;
   a housing for supporting said first receiving transducer, said second receiving transducer and said emitter; and
   an emitter support member by which said ultrasonic emitter is movably supported relative to said housing and for biasing against the object to be tested.

26. A sensing device as set forth in claim 25, further comprising a lateral buffer which is connected to said housing in a manner to surround said ultrasonic emitter and isolate the same from said housing.

27. A sensing device as set forth in claim 25, further comprising a first adjuster connected to said first receiving transducer and said housing such that said first receiving transducer is adjustable relative to said housing and a second adjuster connected to said second receiving transducer and said housing such that said second receiving transducer is adjustable relative to said housing.

* * * * *